US006511837B2

(12) United States Patent
Tsutsumi

(10) Patent No.: US 6,511,837 B2
(45) Date of Patent: Jan. 28, 2003

(54) LIPOLYTIC ENZYMES

(75) Inventor: Noriko Tsutsumi, Chiba-ken (JP)

(73) Assignee: Novozymes A/s, Bagsvaerd (DK)

( * ) Notice: Subject to any disclaimer, the term of this patent is extended or adjusted under 35 U.S.C. 154(b) by 0 days.

(21) Appl. No.: 09/891,735

(22) Filed: Jun. 26, 2001

(65) Prior Publication Data
US 2002/0110854 A1 Aug. 15, 2002

Related U.S. Application Data
(60) Provisional application No. 60/215,277, filed on Jun. 30, 2000.

(30) Foreign Application Priority Data

Jun. 26, 2000 (DK) ........................................ 2000 00991

(51) Int. Cl.[7] ............................. C12N 9/20; C07H 21/04
(52) U.S. Cl. ............... 435/198; 435/254.21; 435/254.3; 435/254.6; 435/254.7; 435/320.1; 536/23.2; 536/23.7; 536/23.74

(58) Field of Search ............................. 435/198, 254.21, 435/254.3, 254.6, 254.7, 320.1; 536/23.2, 23.7, 23.74

(56) References Cited

U.S. PATENT DOCUMENTS 5,830,736 A  11/1998  Oxenbøll et al. ........... 435/198

FOREIGN PATENT DOCUMENTS

WO   WO 98/26057   6/1998

*Primary Examiner*—Nashaat T. Nashed
(74) *Attorney, Agent, or Firm*—Jason I. Garbell

(57) ABSTRACT

The present invention relates to lipolytic enzymes and DNA sequences encoding same. More specifically, the present invention relates to the lipolytic enzyme and DNA encoding same isolated from *Fusarium culmorum* CBS 513.94 and analogues thereof.

6 Claims, No Drawings

LIPOLYTIC ENZYMES

CROSS-REFERENCE TO RELATED APPLICATIONS

This application claims under 35 U.S.C. 119 priority from Danish application no. PA 2000 00991, filed Jun. 26, 2000, and the benefit of U.S. provisional application no. 60/215,277, filed Jun. 30, 2000, the contents of which are fully incorporated herein by reference.

FIELD OF THE INVENTION

The present invention relates to a nucleic acid sequence encoding lipolytic enzymes from *Fusarium culmorum*, as well as a recombinant method of producing the lipolytic enzymes.

BACKGROUND OF THE INVENTION

Lipolytic enzymes (such as lipases and phospholipases) are known to be useful, e.g., in baking and detergents. A lipolytic enzyme from *Fusarium culmorum* CBS 513.94 and its N-terminal sequence are disclosed in U.S. Pat. No. 5,830,736. A lipase/phospholipase from *Fusarium oxysporum* and its sequence are disclosed in WO 98/26057.

The enzyme yield of the wild-type strain is very low, and recombinant productions promises to be an economical way of producing the enzyme.

SUMMARY OF THE INVENTION

The inventors have isolated a gene encoding a lipolytic enzyme from *Fusarium culmorum* CBS 513.94 and cloned it into an *E. coli* strain. Accordingly, the invention provides an isolated DNA sequence encoding a lipolytic enzyme.

The nucleic acid sequence of the invention may comprise a nucleic acid sequence which encodes a lipolytic enzyme and comprises:

a) the DNA sequence encoding a mature lipolytic enzyme cloned into a plasmid present in *Escherichia coli* DSM 13537, b) the DNA sequence encoding a mature lipolytic enzyme shown in SEQ ID NO: 1, or c) an analogue of the DNA sequence defined in a) or b) which i) has at least 80% homology with said DNA sequence, or ii) hybridizes at high stringency with said DNA sequence, its complementary strand or a subsequence thereof.

Other aspects of the invention provide a recombinant expression vector comprising the DNA sequence, and a cell transformed with the DNA sequence or the recombinant expression vector. The invention also provides a recombinant methods of producing the lipolytic enzyme.

A comparison with full-length prior-art sequences shows that the mature amino acid sequence of the lipolytic enzyme from *Fusarium culmorum* has 84% homology with the lipase/phospholipase from *Fusarium oxysporum* described above, and the corresponding DNA sequences show 79% homology.

DETAILED DESCRIPTION OF THE INVENTION

Genomic DNA Source

The DNA sequence of the invention may be derived of *Escherichia coli* DSM 13537 which contains a gene encoding the lipolytic enzyme.

*E. coli* DSM 15357 was deposited by the inventors on Jun. 15, 2000 under the terms of the Budapest Treaty with the DSMZ—Deutshe Sammiung von Microorganismen und Zelikulturen GmbH, Mascheroder Weg 1b, D-38124 Braunschweig DE, Germany.

Lipolytic Enzyme

The lipolytic enzyme encoded by the DNA sequence of the invention is able to hydrolyze carboxylic ester bonds and is classified as EC 3.1.1 according to Enzyme Nomenclature 1992, Academic Press, Inc. The enzyme has lipase (triacylglycerol lipase) activity (EC 3.1.1.3) and may also have phospholipase activity.

Further properties of the lipolytic enzyme are described in U.S. Pat. No. 5,830,736.

Recombinant Expression Vector

The expression vector of the invention typically includes control sequences encoding a promoter, operator, ribosome binding site, translation initiation signal, and, optionally, a selectable marker, a transcription terminator, a repressor gene or various activator genes. The vector may be an autonomously replicating vector, or it may be integrated into the host cell genome.

Production by Cultivation of Transformant

The lipolytic enzyme of the invention may be produced by transforming a suitable host cell with a DNA sequence encoding the lipolytic enzyme, cultivating the transformed organism under conditions permitting the production of the enzyme, and recovering the enzyme from the culture.

The host organism is preferably a eukaryotic cell, in particular a fungal cell, such as a yeast cell or a filamentous fungal cell, e.g. a strain of Aspergillus, Fusarium, Trichoderma or Saccharomyces, particularly *A. niger, A. oryzae, F. graminearum, F. sambucinum, F. cerealis* or *S. cerevisiae*. The production of the lipolytic enzyme in such host organisms may be done by the general methods described in EP 238,023 (Novo Nordisk), WO 96/00787 (Novo Nordisk) or EP 244,234 (Alko).

Hybridization

The hybridization is used to indicate that a given DNA sequence is analogous to a nucleotide probe corresponding to a DNA sequence of the invention. The hybridization conditions are described in detail below.

Suitable conditions for determining hybridization between a nucleotide probe and a homologous DNA or RNA sequence involves presoaking of the filter containing the DNA fragments or RNA to hybridize in 5× SSC (standard saline citrate) for 10 min, and prehybridization of the filter in a solution of 5× SSC (Sambrook et al. 1989), 5× Denhardt's solution (Sambrook et al. 1989), 0.5% SDS and 100 µg/ml of denatured sonicated salmon sperm DNA (Sambrook et al. 1989), followed by hybridization in the same solution containing a random-primed (Feinberg, A. P. and Vogelstein, B. (1983) *Anal. Biochem.* 132:6–13), $^{32}$P-dCTP-labeled (specific activity >1×10 cpm/µg) probe for 12 hours at approx. 45° C. The filter is then washed two times for 30 minutes in 2× SSC, 0.5% SDS at a temperature of at least 55° C., more preferably at least 60° C., more preferably at least 65° C., even more preferably at least 70° C., especially at least 75° C.

Molecules to which the oligonucleotide probe hybridizes under these conditions are detected using an x-ray film.

Alignment and Homology

The present invention also includes lipolytic enzymes and nucleotide sequences encoding same that have homology to the disclosed sequences. More preferably, the lipolytic enzymes and the nucleotide sequences of the invention may have homologies to the disclosed sequences of at least 85%, at least 90% or at least 95%, e.g. at least 96%, at least 97%, at least 98%.

For purposes of the present invention, alignments of sequences and calculation of homology scores were done using a Needleman-Wunsch alignment (i.e. global alignment), useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment is from the FASTA package version v20u6 (W. R. Pearson and D. J. Lipman (1988), "Improved Tools for Biological Sequence Analysis", PNAS 85:2444–2448, and W. R. Pearson (1990) "Rapid and Sensitive Sequence Comparison with FASTP and FASTA", Methods in Enzymology, 183:63–98).

Lipase Activity (LU)

A substrate for lipase is prepared an emulsion of 5% by volume of tributyrin (glycerin tributyrate) using 0.1% gum Arabic as emulsifier. The hydrolysis of tributyrin at 30° C. at pH 7 is followed in a pH-stat titration experiment. One unit of lipase activity (1 LU) equals the amount of enzyme capable of releasing 1 μmol butyric acid/min at the standard conditions. 1 KLU=1000 LU.

Use of Lipolytic Enzyme

The lipolytic enzyme of the invention can be used in various industrial application of lipolytic enzymes, e.g. in baking, detergents, diglyceride synthesis (EP 307154), acidolysis, interesterification (WO 8802775), ester hydrolysis, oil degumming (JP-A 2-153997, U.S. Pat. No. 5,264,367), production of lysolecithin (JP patent 2794574, JP-B 6-087751) and in the process described in PCT/DK 00/00109.

Use in Baking

The lipolytic enzyme of the invention can be used in the preparation of dough, bread and cakes, e.g. to improve the elasticity of the bread or cake. Thus, the lipolytic enzyme can be used in a process for making bread, comprising adding the lipolytic enzyme to the ingredients of a dough, kneading the dough and baking the dough to make the bread. This can be done in analogy with WO 9404035 and EP 585988.

Use in Detergent

The variant may be used as a detergent additive, e.g. at a concentration (expressed as pure enzyme protein) of 0.001–10 (e.g. 0.01–1) mg per gram of detergent or 0.001–100 (e.g. 0.01–10) mg per liter of wash liquor.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations. In a laundry detergent, the variant may be effective for the removal of fatty stains, for whiteness maintenance and for dingy cleanup. A laundry detergent composition may be formulated as described in WO 97/04079, WO 97/07202, WO 97/41212, PCT/DK WO 98/08939 and WO 97/43375.

The detergent composition of the invention may particularly be formulated for hand or machine dishwashing operations. e.g. as described in GB 2,247,025 (Unilever) or WO 99/01531 (Procter & Gamble). In a dishwashing composition, the variant may be effective for removal of greasy/oily stains, for prevention of the staining/discoloration of the dishware and plastic components of the dishwasher by highly colored components and the avoidance of lime soap deposits on the dishware.

MATERIALS AND METHODS

Methods

Unless otherwise stated, DNA manipulations and transformations were performed using standard methods of molecular biology as described in Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology", John Wiley and Sons, 1995; Harwood, C. R., and Cutting, S. M. (eds.) "Molecular Biological Methods for Bacillus". John Wiley and Sons, 1990.

Enzymes

Enzymes for DNA manipulations (e.g. restriction endonucleases, ligases etc.) are obtainable from New England Biolabs, Inc. and were used according to the manufacturer's instructions.

Plasmids/Vectors pT7Blue (Invitrogen, Netherlands)

Cloning

LA PCR™ in vitro Cloning Kit (TaKaRa) was used for cloning and was used according to the manufacturer's instructions.

Microbial Strains

*E. coli* JM109 (TOYOBO, Japan)

*E. coli* JM110 (Invitrogen)

*E.coli* DB6507 (F,pnrF74::Tn5,seupE44, lacY1, ara-14, galK2, xyl-5, mtl-1, leuB6, proA2, hsdS20, recA13, rpsL20, thi-1, lambda-)

*A. oryzae* BECh-2 is described in Danish patent application PA 1999 01726. It is a mutant of JaL 228 (described in WO 98/12300) which is a mutant of IFO 4177.

Reagents

Media and Reagents

Cove: 342.3 g/L Sucrose, 20 ml/L COVE salt solution, 10 mM Acetamide, 30 g/L noble agar.

Cove-2: 30 g/L Sucrose, 20 mil/L COVE salt solution, 10 mM, Acetamide, 30 g/L noble agar.

Cove salt solution: per liter 26 g KCl, 26 g MgSO4-7aq, 76 g KH2PO4, 50 ml Cove trace metals.

Cove trace metals: per liter 0.04 g NaB4O7-10aq, 0.4 g CuSO4-5aq, 1.2 g FeSO4-7aq, 0.7 g MnSO4-aq, 0.7 g Na2MoO2-2aq, 0.7 g ZnSO4-7aq.

AMG trace metals: per liter 14.3 g ZnSO4-7aq, 2.5 g CuSO4-5aq, 0.5 g NiCl2, 13.8 g FeSO4, 8.5 g MnSO4, 3.0 g citric acid.

YPG: 4 g/L Yeast extract, 1 g/L KH2PO4, 0.5 g/L MgSO4-7aq, 5 g/L Glucose, pH 6.0.

STC: 0.8 M Sorbitol, 25 mM Tris pH 8, 25 mM CaCl2.

STPC: 40% PEG4000 in STC buffer.

Cove top agarose: 342.3 g/L Sucrose, 20 ml/L COVE salt solution, 10 mM Acetamide, 10 g/L low melt agarose.

MS-9: per liter 30 g soybean powder, 20 g glycerol, pH 6.0.

MDU-pH5: per liter 45 g maltose-1aq, 7 g yeast extract, 12 g KH2PO4, 1 g MgSO4-7aq, 2 g K2SO4, 0.5 ml AMG trace metal solution and 25 g 2-morpholinoethanesulfonic acid, pH 5.0.

EXAMPLES

Example 1

Cloning and Expression of Lipase Gene from *Fusarium culmorum*

Transformation in Aspergillus Strain

*Aspergillus oryzae* strain BECh-2 was inoculated to 100 ml of YPG medium and incubated for 16 hrs at 32° C. at 120 rpm. Pellets were collected and washed with 0.6 M KCl, and resuspended 20 ml 0.6 M KCl containing a commercial β-glucanase product (Glucanex, product of Novo Nordisk A/S) at the concentration of 30 μl/ml. Cultures were incubated at 32° C. at 60 rpm until protoplasts formed, then washed with STC buffer twice. The protoplasts were counted with a hematometer and resuspended in an 8:2:0.1 solution of STC:STPC:DMSO to a final concentration of 2.5×10e7 protoplasts/ml. About 3 μg of DNA was added to 100 μl of protoplasts solution, mixed gently and incubated on ice for 30 min. One ml of SPTC was added and incubated 30 min at 37° C. After the addition of 10 ml of 50° C. Cove top agarose, the reaction was poured onto Cove agar plate. Transformation plates were incubated at 32° C. for 5 days.

PCR Screening of Lipase

A strain of *Fusarium culmorum* was used as a genomic DNA supplier.

```
12N1: 5'-actgaacagttggacagccgtttccgctgc-3'          (SEQ ID NO: 4)

12C2: 5'-ccaggctggtggagagttccgcgttacgaacg-3'       (SEQ ID NO: 5)
```

Obtained fragments were purified by GFX™ PCR DNA and Gel Band Purification kit (amersham pharmacia biotech) and sequenced with each primer which amplified the fragment. Their sequence were compared to the *Fusarium oxysporum* lipase, showing that the amplified DNA covered N-terminal and C-terminasl part of the lipase.

The fidelity of taq polymerase is not so good so in order to get the right sequence whole gene was amplified the following primers.

```
12-N(Bcl): 5'-ttgtctgtgatcatgcgtctcctgtcactcctc-3'           (SEQ ID NO: 6)

12-C(Sal): 5'-ttagtgcgtaaacagctgactatgatgagcggctggcgtgagtc-3'  (SEQ ID NO: 7)
```

PCR reactions on *Fusarium culmorum* genomic DNA was done with two following primer set: lip2/lip21 designed based upon the alignment 3 lipases from Fusarium.

```
lip2(SEQ ID NO: 2)
tytayathcarcaygg-3' lip21(SEQ ID NO: 3)
5'-tciswigtytgickrtaiccraa-3'
```

Reaction components (6 ng/μl of genomic DNA, 250 mM dNTP each, primer 250 nM each, 0.1 U/μl in Taq polymerase in 1× buffer (Roche Diagnostics, Japan)) were mixed and submitted for PCR under the following conditions.

| Step | Temperature | Time |
| --- | --- | --- |
| 1 | 94° C. | 1 min |
| 2 | 50° C. | 1 min |
| 3 | 72° C. | 2 min |
| 4 | 72° C. | 10 min |
| 5 | 4° C. | forever |

Steps 1 to 3 were repeated 30 times.

0.7 kbp of fragment was amplified. It was gel-purified with GFX™ PCR DNA and Gel Band Purification kit (amersham pharmacia biotech) and ligated into a pT7Blue vector with ligation high (TOYOBO, Japan). The ligation mixtures were transformed into *E. coli* JM109. The resultant plasmids, pT12-0221 was sequenced and compared to the *Fusarium oxysporum* lipase, showing that a clone encodes the internal part of the lipase.

Cloning of Lipase Gene

In order to clone the missing part of the lipase gene, LA PCR™ in vitro Cloning Kit (TaKaRa) was used for genome walking. 0.5 kbp of DNA fragment corresponding to N-terminal region was obtained from BamH I digested genome ligated to Sau3A I cassette of the kit with 12N1 primer. 1.8 kb of DNA fragment corresponding to C-terminal region was obtained from Bgl II digested genome ligated to Sau3A I cassette of the kit with 12C2 primer.

Reaction components (6 ng/μl of genomic DNA, 250 mM dNTP each, primer 250 nM each, 0.05 U/μl of Expand high fidelity polymerase in 1× buffer (Roche Diagnostics, Japan)) were mixed and submitted for PCR under the following conditions.

| Step | Temperature | Time |
| --- | --- | --- |
| 1 | 94° C. | 2 min |
| 2 | 94° C. | 10 sec |
| 3 | 55° C. | 30 sec |
| 4 | 68° C. | 45 sec |
| step 2–4 repeat 10 times | | |
| 5 | 94° C. | 10 sec |
| 6 | 55° C. | 30 sec |
| 7 | 68° C. | 45 sec +20 sec/cycle |
| step 5–7, repeat 20 times | | |
| 8 | 68° C. | 7 min |
| 7 | 4° C. | forever |

An amplified DNA fragment was gel-purified with GFX™ PCR DNA and Gel Band Purification kit (amersham pharmacia biotech) and ligated into a pT7Blue vector with ligation high (TOYOBO, Japan). The ligation mixtures were transformed into *E. coli* JM109. The resultant plasmids, pT12-1, pT12-2, pT12-3, and pT12-4, were sequenced and all of them are identical. The sequence is defined as *Fusarium culmorum* lipase DNA sequence.

Expression of Lipase Gene in *Aspergillus oryzae*.

The plasmid pT12-6 was transformed to JM110 and non-methylated pT12-6 was extracted. The lipase gene was digested from non-methylated pT12-6 with Bcl I and Sal I into T-vector and ligated into the BamH I and XhoI sites in the Aspergillus expression cassette pMT2188 which has *Aspergillus niger* neutral amylase promoter, *Aspergillus nidulans* TPI leader sequences, *Aspergillus niger* glucoamylase terminator and *Aspergillus nidulans* amdS gene as a marker and *Saccharomyces cerevisiae* URA3 gene as a marker for a plasmid construction. The ligation mixture was transformed *E. coli* 6507 by electroporation and the resultant plasmid was pNL12-***.

pNL12-*** was transformed into *Aspergillus oryzae* BECh-2. The selected transformants were inoculated in 100 ml of MS-9 media and cultivated at 30° C. for 1 day. 3 ml of grown cell in MS-9 medium was inoculated to 100 ml of MDU-2BP medium and cultivated at 32° C. for 3 days. The supernatant was obtained by centrifugation.

The lipase productivity of selected transformants was determined as LU activity.

```
12N1:      5'-actgaacagttggacagccgtttccgctgc-3'                   (SEQ ID NO: 4)

12C2:      5'-ccaggctggtggagagttccgcgttacgaacg-3'                 (SEQ ID NO: 5)

12-N(Bcl): 5'-ttgtctgtgatcatgcgtctcctgtcactcctc-3'                (SEQ ID NO: 6)

12-C(Sal): 5'-ttagtgcgtaaacagctgactatgatgagcggctggcgtgagtc-3'     (SEQ ID NO: 7)
```

What is claimed is:

1. A nucleic acid sequence which comprises:
   a) a DNA sequence encoding a mature lipolytic enzyme cloned into a plasmid present in *Escherichia coli* DSM 13537,
   b) a DNA sequence shown in SEQ ID NO: 1,
   c) an analogue of the sequence defined in a) or b) which encodes a lipolytic enzyme, wherein the analogue
      i) has at least 95% homology with said a) or b), or
      ii) hybridizes with a complementary strand of said a) or b) under hybridization conditions comprising prehybridizing in a solution of 5×SSC, 5×Denhardt's solution, 0.5% SDS and 100 µg/ml of denatured sonicated salmon sperm DNA, followed by hybridization in the same solution for 12 hours at approx.

45° C., followed by washing in 2×SSC, 0.5% SDS for 30 minutes at a temperature of at least 70° C., or d) a complementary strand of said a), b) or c).

2. A nucleic acid construct comprising the nucleic acid sequence of claim 1 operably linked to one or more control sequences that direct the expression of the lipolytic enzyme in a suitable expression host.

3. A recombinant expression vector comprising the nucleic acid sequence of claim 1, a promoter, and transcriptional and translational stop signals.

4. A recombinant host cell comprising the nucleic acid construct of claim 2.

5. A method for producing a lipolytic enzyme comprising cultivating the host cell of claim 4 under conditions conducive to production of the lipolytic enzyme, and recovering the lipolytic enzyme.

6. The nucleic acid sequence of claim 1, wherein the analogue has at least 95% homology with said a) or b).

* * * * *

SEQUENCE LISTING

<160> NUMBER OF SEQ ID NOS: 7

<210> SEQ ID NO 1
<211> LENGTH: 1159
<212> TYPE: DNA
<213> ORGANISM: Fusarium sp.

<400> SEQUENCE: 1

```
atgcgtctcc tgtcactcct ctcagttgtc acccttgtgg tagccagccc tctgagcgtt      60
gaagaatacg ccaaggctct cgatgaacga ggtacacacg atcatcattc ctataacaaa     120
ctccatactc acaaagtctc tagctgtctc tgtctccacc accgactttg gcaatttcaa     180
gttctacatc cagcacggcg ccgcagcata ctgcaactcc gaagccccgg ccggtgcaaa     240
ggtcacctgc agcggaaacg gctgtccaac tgttcagtcc aacggtgtta ccatcgtggc     300
atccttcacg taagtcccac ccgcacaaa cacatcacca actccaagct tacacgtttc     360
tctcagtgga tccaagactg gaatcggcgg ctacgtcgct acagacccta cacgcaagga     420
gatcgtcgtc tcgttccgtg gtagcatcaa catccgcaac tggcttacca acctcgactt     480
cgaccaggac gactgcagcc tgacctcggg ctgtggtgtt cactcaggct tccagaaagc     540
ctggaacgag atctcagccg cggcaaccgc cgctgtcgca aaggcccgca aggcaaaccc     600
ttcgttcaag gtcgtctccg taggtcactc cctgggtggt gctgtagcta cactggcagg     660
cgcgaaccta cgagttggtg aacaccccct tgacatttac acctacggtt caccccgagt     720
tggaaacaca cagctcgctg cttttgtctc gaaccaggct ggtggagagt tccgcgttac     780
gaacgccaaa gaccccgtgc ctcgtctccc ccctctgatc tttggatacc gacacacatc     840
ccccgagtac tggctgtctg gcagcggagg tgacaagatc gactacacca tcaacgatgt     900
caaggtctgt gaaggtgccg ccaacctcca gtgcaacggt ggaacactcg gattggatat     960
cgatgcccat ctccactact tccaggcaac tgatgcttgc tctgctggcg gcatctcgtg    1020
gagaagatac aggagcgcca agcgtgagag catctcagag agggctacca tgaccgacgc    1080
cgagctcgag aagaagctca acagctatgt tgagatggat aaggagtata tcaagactca    1140
cgccagccgc tcatcatag                                                 1159
```

<210> SEQ ID NO 2
<211> LENGTH: 20
<212> TYPE: PRT
<213> ORGANISM: Artificial Sequence
<220> FEATURE:
<223> OTHER INFORMATION: Primer

<400> SEQUENCE: 2

Ala Ala Arg Thr Thr Tyr Thr Ala Tyr Ala Thr His Cys Ala Arg Cys

-continued

```
1               5               10              15
Ala Tyr Gly Gly
            20

<210> SEQ ID NO 3
<211> LENGTH: 23
<212> TYPE: PRT
<213> ORGANISM: Artificial Sequence
<220> FEATURE:
<223> OTHER INFORMATION: Primer

<400> SEQUENCE: 3

Thr Cys Ile Ser Trp Ile Gly Thr Tyr Thr Gly Ile Cys Lys Arg Thr
1               5                   10                  15

Ala Ile Cys Cys Arg Ala Ala
            20

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
actgaacagt tggacagccg tttccgctgc                                    30

<210> SEQ ID NO 5
<211> LENGTH: 32
<212> TYPE: DNA
<213> ORGANISM: Artificial Sequence
<220> FEATURE:
<223> OTHER INFORMATION: Primer

<400> SEQUENCE: 5
ccaggctggt ggagagttcc gcgttacgaa cg                                 32

<210> SEQ ID NO 6
<211> LENGTH: 33
<212> TYPE: DNA
<213> ORGANISM: Artificial Sequence
<220> FEATURE:
<223> OTHER INFORMATION: Primer

<400> SEQUENCE: 6
ttgtctgtga tcatgcgtct cctgtcactc ctc                                33

<210> SEQ ID NO 7
<211> LENGTH: 44
<212> TYPE: DNA
<213> ORGANISM: Artificial Sequence
<220> FEATURE:
<223> OTHER INFORMATION: Primer

<400> SEQUENCE: 7
ttagtgcgta aacagctgac tatgatgagc ggctggcgtg agtc                    44
```